(12) United States Patent
Abe (10) Patent No.: US 11,926,718 B2
(45) Date of Patent: Mar. 12, 2024

(54) RESIN BEADS, METHOD FOR PRODUCING RESIN BEADS, AND PRODUCT USING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 18/042,739

(22) PCT Filed: Aug. 10, 2021

(86) PCT No.: PCT/JP2021/029501
§ 371 (c)(1),
(2) Date: Feb. 23, 2023

(87) PCT Pub. No.: WO2022/050004
PCT Pub. Date: Mar. 10, 2022

(65) Prior Publication Data
US 2023/0303782 A1    Sep. 28, 2023

(30) Foreign Application Priority Data
Sep. 1, 2020   (JP) .................. 2020-147044

(51) Int. Cl.
C08J 3/14        (2006.01)
C08L 1/12        (2006.01)
C08L 1/14        (2006.01)
C08L 1/16        (2006.01)

(52) U.S. Cl.
CPC .    *C08J 3/14* (2013.01); *C08L 1/12* (2013.01); *C08L 1/14* (2013.01); *C08L 1/16* (2013.01); *C08J 2301/10* (2013.01); *C08J 2301/16* (2013.01); *C08L 2201/06* (2013.01); *C08L 2205/18* (2013.01)

(58) Field of Classification Search
CPC ...................................... C08L 1/02; C09J 3/14
See application file for complete search history.

(56) References Cited

U.S. PATENT DOCUMENTS

| 4,663,447 | A | 5/1987 | Yamazaki et al. |
| 4,968,350 | A | 11/1990 | Bindschaedler et al. |
| 5,244,734 | A * | 9/1993 | Okuma .................. C08B 16/00 428/407 |
| 5,245,024 | A | 9/1993 | Scarpa et al. |
| 5,972,507 | A | 10/1999 | Morimoto et al. |
| 6,225,461 | B1 | 5/2001 | Akimoto et al. |
| 6,541,627 | B1 * | 4/2003 | Ono .......................... C08J 3/09 536/124 |
| 6,571,802 | B1 | 6/2003 | Yamashita |
| 8,192,748 | B2 | 6/2012 | Kuroda |
| 11,548,999 | B2 * | 1/2023 | Abe ......................... C08L 1/12 |
| 11,628,134 | B2 | 4/2023 | Kobayashi et al. |
| 2003/0012941 | A1 | 1/2003 | Fujita et al. |
| 2005/0118121 | A1 | 6/2005 | Kuroda |
| 2005/0203278 | A1 | 9/2005 | McCreight et al. |
| 2008/0131597 | A1 | 6/2008 | Takehara et al. |
| 2009/0044942 | A1 * | 2/2009 | Gupta .................. C09K 8/5751 507/214 |
| 2009/0280186 | A1 * | 11/2009 | Yaginuma ............ A61K 9/1623 424/494 |
| 2010/0087552 | A1 | 4/2010 | Shiomi et al. |

(Continued)

FOREIGN PATENT DOCUMENTS

CN    102911379    2/2013
EP    0309527    4/1989

(Continued)

OTHER PUBLICATIONS

International Search Report, issued in the corresponding PCT application No. PCT/JP2021/029501, dated Sep. 21, 2021, 7 pages (including machine translation).
International Search Report, issued in the related PCT application No. PCT/JP2020/026551, dated Sep. 24, 2020, 7 pages (including translation).
Extended European Search Report, issued in the related European Patent Application No. 20837372.0, dated Jul. 29, 2022, 10 pages.
"Novel colored complex cellulose beads", Society of Cosmetic Scientists, 2003, 1 page.
Brazilian Office Action, issued in the related Brazilian Patent Application No. 112022000453-2, dated Jun. 10, 2022, 8 pages.

(Continued)

*Primary Examiner* — Liam J Heincer
(74) *Attorney, Agent, or Firm* — Hamre, Schumann, Mueller & Larson, P.C.

(57) ABSTRACT

The present invention provides resin beads that can provide various types of products, such as a cosmetic having excellent tactile impression, spreadability on the skin, and transparency, that can be substituted for resin particles composed of a synthetic material derived from petroleum, and that have favorable biodegradability, and the present invention also provides various types of products, such as a cosmetic using the resin beads. The resin beads are formed with a resin containing cellulose as a main component. The resin beads have a cumulative 50% particle size on a volume basis of 50 μm or smaller, a degree of sphericity of 0.7 to 1.0, a degree of surface smoothness of 70 to 100%, a degree of solidity of 50 to 100%, and a biodegradation rate for 5 days, as measured in accordance with JIS K6950:2000 (ISO 14851:1999), of 20% or more, and the content of the cellulose in the resin is 90 to 100% by mass. In addition, the present invention provides a product of any one of a cosmetic, a dermatological preparation, a paint, a shaped article, a film, a coating agent, and a resin composition which contain the resin beads.

7 Claims, 2 Drawing Sheets

(56) References Cited

U.S. PATENT DOCUMENTS

| | | | |
|---|---|---|---|
| 2010/0178332 A1* | 7/2010 | Kakizawa | A61K 9/2077 |
| | | | 424/490 |
| 2011/0282049 A1 | 11/2011 | Shelton et al. | |
| 2016/0303032 A1 | 10/2016 | Kamei | |
| 2020/0179261 A1* | 6/2020 | Kobayashi | A61K 8/36 |
| 2020/0299488 A1* | 9/2020 | Kobayashi | A61K 8/0241 |
| 2022/0025131 A1* | 1/2022 | Shibata | C08J 3/16 |
| 2022/0142900 A1* | 5/2022 | Kobayashi | C08J 3/12 |
| 2022/0154356 A1 | 5/2022 | Manabe | |
| 2022/0267573 A1 | 8/2022 | Abe | |
| 2022/0275163 A1* | 9/2022 | Shibata | C08J 9/28 |
| 2023/0136180 A1* | 5/2023 | Abe | C08J 3/14 |
| | | | 424/401 |

FOREIGN PATENT DOCUMENTS

| | | |
|---|---|---|
| EP | 0750007 | 12/1996 |
| EP | 3613794 | 2/2020 |
| EP | 3943530 | 1/2022 |
| EP | 3998300 | 5/2022 |
| EP | 4116357 | 1/2023 |
| EP | 4209514 | 7/2023 |
| EP | 4234043 | 8/2023 |
| JP | 49-019183 | 2/1974 |
| JP | 50-041954 | 4/1975 |
| JP | 51-090352 | 8/1976 |
| JP | 55-028763 | 2/1980 |
| JP | 59-219333 | 12/1984 |
| JP | 60-155245 | 8/1985 |
| JP | 62-253601 | 11/1987 |
| JP | 63-068645 | 3/1988 |
| JP | 63-095237 | 4/1988 |
| JP | 06-254373 | 9/1994 |
| JP | 11-181147 | 7/1999 |
| JP | 2931810 | 8/1999 |
| JP | 11-279201 | 10/1999 |
| JP | 2000-309503 | 11/2000 |
| JP | 2000-309508 | 11/2000 |
| JP | 2002-205917 | 7/2002 |
| JP | 2002-363445 | 12/2002 |
| JP | 2003-146829 | 5/2003 |
| JP | 2005-264120 | 9/2005 |
| JP | 2006-131875 | 5/2006 |
| JP | 2006-523752 | 10/2006 |
| JP | 2006-328245 | 12/2006 |
| JP | 2007-528436 | 10/2007 |
| JP | 4076955 | 4/2008 |
| JP | 2012-092191 | 5/2012 |
| JP | 2013-221000 | 10/2013 |
| JP | 2014-224183 | 12/2014 |
| JP | 2015-117190 | 6/2015 |
| JP | 2017-052961 | 3/2017 |
| JP | 2018-008392 | 1/2018 |
| JP | 2018-052909 | 4/2018 |
| JP | 2018-127579 | 8/2018 |
| JP | 2019-031631 | 2/2019 |
| JP | 6609726 | 11/2019 |
| JP | 2020-075878 | 5/2020 |
| JP | 6694559 | 5/2020 |
| JP | 2020-132616 | 8/2020 |
| JP | 2020-152851 | 9/2020 |
| WO | 88/08011 | 10/1988 |
| WO | 1999/028350 | 6/1999 |
| WO | 2003/075863 | 9/2003 |
| WO | 2004/083253 | 9/2004 |
| WO | 2009/123148 | 10/2009 |
| WO | 2015/029790 | 3/2015 |
| WO | 2016/013568 | 1/2016 |
| WO | 2019/156116 | 8/2019 |
| WO | 2020/188698 | 9/2020 |

OTHER PUBLICATIONS

International Search Report, issued in the related PCT application No. PCT/JP2021/007183, dated May 18, 2021, 5 pages (including machine translation).

"Measuring method for specific gravity of solid", JIS Handbook 31 Chemical analysis, pp. 751-755, Japanese Standards Association, Apr. 20, 1997, cited in the Notice of Reasons for Revocation (A concise explanation of relevance provided in Notice of Reasons for Revocation for JP patent application 2020-036983, dated Aug. 20, 2021).

"Technical Data Sheet, Cellulose Acetate Propionate CAP-482-0.5", Eastman, cited in the Notice of Reasons for Revocation (dated Mar. 30, 2022), 4 pages, 2021.

Notice of Reasons for Revocation of JP patent 6779400 (JP patent application 2020-036983), issued in the Trial/Appeal Opposition No. JP 2021-700373, dated Aug. 20, 2021, 41 pages (including machine translation).

Notice of Reasons for Revocation of JP patent 6779400 (JP patent application 2020-036983) with allowance of amendments, issued in the Trial/Appeal Opposition No. JP 2021-700373, dated Mar. 30, 2022, 57 pages (including machine translation).

El-Habashy et al., "Ethyl cellulose nanoparticles as a platform to decrease ulcerogenic potential of piroxicam: formulation and in vitro/in vivo evaluation", International Journal of Nanomedicine, Original Research, 2016, pp. 2369-2380.

Scarfato et al., "Quercetin microspheres by solvent evaporation: Preparation, characterization and release behavior", Journal of Applied Science, vol. 109, 2008, pp. 2994-3001.

International Search Report, issued in the related PCT application No. PCT/JP2021/034810, dated Nov. 30, 2021, 5 pages (including translation).

Extended European Search Report, issued in the corresponding European Patent Application No. 21864062.1, dated Oct. 13, 2023, 9 pages.

Extended European Search Report, issued in the corresponding European Patent Application No. 21764155.4, dated Oct. 13, 2023, 8 pages.

Takashi Abe, U.S. Appl. No. 18/257,531, filed Jun. 14, 2023, titled "Resin Beads, Method for Producing Resin Beads, and Product Using Resin Beads", 48 pages.

U.S. Appl. No. 17/597,111, filed Dec. 27, 2021, 2022/0267573, (now U.S. Pat. No. 11,548,999 on Jan. 10, 2023)

U.S. Appl. No. 17/905,233, filed Aug. 29, 2022, 2023/0136180.

U.S. Appl. No. 18/257,531, filed Jun. 14, 2023, not published yet.

* cited by examiner

RESIN BEADS, METHOD FOR PRODUCING RESIN BEADS, AND PRODUCT USING RESIN BEADS

TECHNICAL FIELD

The present invention relates to resin beads formed with a resin containing cellulose as a main component, a method for producing the resin beads, and products, such as a cosmetic, obtained using the resin beads.

BACKGROUND ART

In the past, resin beads have been used in various fields, such as a matting agent, a slipping agent, and an antiblocking agent, from the properties derived from the spherical shape. Further, various resin powders (resin particles), such as resin beads, have been used in order to improve the properties, such as spreadability of cosmetics for makeup. However, materials for forming resin beads to be blended in cosmetics have been changed from synthetic materials derived from petroleum to natural materials due to the problems and the like, such as marine pollution caused by microplastics, in recent years.

For example, powdery cellulose useful as a scrubbing agent has been proposed as spherical resin particles composed of a natural material (Patent Literature 1). Further, cellulose derivative fine particles (Patent Literature 2) which are used for a diagnostic drug and a spherical cellulose powder (Patent Literature 3) which is used for cosmetics have been proposed. Furthermore, porous cellulose particles (Patent Literatures 4 to 6) which are used as a filler for chromatography, and the like have been proposed.

CITATION LIST

Patent Literature

Patent Literature 1: Japanese Patent Laid-Open No. 2018-052909
Patent Literature 2: International Publication No. WO 2009/123148
Patent Literature 3: Japanese Patent Laid-Open No. 2013-221000
Patent Literature 4: International Publication No. WO 2016/013568
Patent Literature 5: International Publication No. WO 2015/029790
Patent Literature 6: Japanese Patent Laid-Open No. 62-253601

SUMMARY OF INVENTION

Technical Problem

However, the powdery cellulose and the like proposed in Patent Literatures 1, 2, 4, and 5 do not have a suitable particle size as a material to be blended in cosmetics for makeup or skin care. In addition, copper ammonia needs to be used when the cellulose derivative fine particles proposed in Patent Literature 2 are produced, and therefore the cellulose derivative fine particles cannot necessarily be said to be suitable as a material for cosmetics in which heavy metals are desired to be reduced as much as possible.

Further, the spherical cellulose powder and the like proposed in Patent Literatures 3 to 5 have a low degree of sphericity, and the particle surface thereof is not so smooth. For this reason, the spreadability on the skin cannot be said to be favorable so much when the spherical cellulose powders and the like are blended in cosmetics, so that rough surfaces have been likely to be felt. In addition, light scattering is likely to occur due to the roughness of the particle surfaces and the non-solid structure, and therefore the feel of the cosmetics has been likely to change significantly accompanying wetting of the powder and use of the powder in a solution.

Furthermore, porous cellulose particles and the like proposed in Patent Literatures 4 to 6 have low strength and are likely to adsorb moisture because they are porous. For this reason, when the porous cellulose particles and the like are blended in cosmetics, the cosmetics themselves are likely to be made unstable, and therefore the porous cellulose particles and the like cannot necessarily be said to be suitable as a material for cosmetics.

The present invention has been completed in view of the problems of such conventional techniques, and an object of the present invention is to provide resin beads that can provide various types of products, such as a cosmetic having excellent tactile impression, spreadability on the skin, and transparency, that can be substituted for resin particles composed of a synthetic material derived from petroleum, and that have favorable biodegradability, and to provide various types of products, such as a cosmetic, using the resin beads. Another object of the present invention is to provide a method for producing resin beads that can provide various types of products, such as a cosmetic having excellent tactile impression, spreadability on the skin, and transparency, that can be substituted for resin particles composed of a synthetic material derived from petroleum, and that have favorable biodegradability.

Solution to Problem

That is, according to the present invention, resin beads, described below, are provided.

[1] Resin beads formed with a resin comprising cellulose as a main component, wherein the resin beads have a cumulative 50% particle size on a volume basis of 50 μm or smaller, a degree of sphericity of 0.7 to 1.0, a degree of surface smoothness of 70 to 100%, a degree of solidity of 50 to 100%, and a biodegradation rate for 5 days, as measured in accordance with JIS K6950:2000 (ISO 14851:1999), of 20% or more, and a content of the cellulose in the resin is 90 to 100% by mass.

[2] The resin beads according to [1], having a cumulative 90% particle size on a volume basis of 40 μm or smaller.

[3] The resin beads according to [1] or [2], having a cumulative 10% particle size on a volume basis of 0.1 μm or larger.

[4] The resin beads according to any one of [1] to [3], wherein a CV value of the particle size is 10 to 90%.

[5] The resin beads according to any one of [1] to [4], comprising at least any one of a pigment and a dye.

[6] The resin beads according to any one of [1] to [5], comprising at least any one of an ultraviolet absorbing agent and an ultraviolet scattering agent.

In addition, according to the present invention, a method for producing resin beads, described below, is provided.

[7] A method for producing resin beads, being a method for producing the resin beads according to any one of [1] to [6], the method comprising: a step of mixing an oil phase comprising a cellulose ester and an organic solvent that dissolves the cellulose ester and has a solubility to 100 g of water at 25° C. of 0.1 to 50.0 g with an aqueous phase comprising a dispersion stabilizer, thereby preparing a suspension comprising oil droplets comprising the cellulose ester and the organic solvent; a step of adding water to the suspension, thereby contracting the oil droplets and forming resin particles; and a step of treating the resin particles under an acidic condition, or an alkaline condition of a pH of 13 or lower, thereby hydrolyzing at least part of ester bonds in the cellulose ester.

[8] The method for producing resin beads according to [7], wherein the water is added to the suspension over 10 minutes or longer.

[9] The method for producing resin beads according to [7] or [8], wherein a liquid amount of the water to be added to the suspension is 0.5 times or more based on a liquid amount of the suspension on a mass basis.

[10] The method for producing resin beads according to any one of [7] to [9], wherein the cellulose ester is at least one selected from the group consisting of a cellulose organic acid ester and a cellulose phosphoric acid ester.

[11] The method for producing resin beads according to any one of [7] to [10], wherein the cellulose ester is at least one selected from the group consisting of cellulose acetate, cellulose propionate, cellulose acetate propionate, cellulose butyrate, and cellulose acetate butyrate.

[12] The method for producing resin beads according to any one of [7] to [11], wherein the dispersion stabilizer is a water-soluble polymer.

[13] The method for producing resin beads according to any one of [7] to [12], wherein the resin particles are treated under a temperature condition of 80° C. or lower, thereby hydrolyzing at least part of the ester bonds in the cellulose ester.

Further, according to the present invention, a product, described below, is provided.

[14] A product of any one of a cosmetic, a dermatological preparation, a paint, a shaped article, a film, a coating agent, and a resin composition each comprising resin beads, wherein
the resin beads are the resin beads according to any one of [1] to [6].

Advantageous Effects of Invention

The present invention can provide: resin beads that can provide various types of products, such as a cosmetic having excellent tactile impression, spreadability on the skin, and transparency, that can be substituted for resin particles composed of a synthetic material derived from petroleum, and that have favorable biodegradability; and various types of products, such as a cosmetic, using the resin beads. Further, the present invention can provide a method for producing resin beads that can provide various types of products, such as a cosmetic having excellent tactile impression, spreadability on the skin, and transparency, that can be substituted for resin particles composed of a synthetic material derived from petroleum, and that have favorable biodegradability.

DESCRIPTION OF EMBODIMENTS

Hereinafter, embodiments of the present invention will be described, but the present invention is not limited to the following embodiments. Note that various physical property values as used herein are values at normal temperature (25° C.) unless otherwise noted.

The present inventors have conducted various studies on resin beads that can provide various types of products, such as a cosmetic imparted with excellent tactile impression, spreadability on the skin, and transparency, that have favorable biodegradability, and that are composed of a natural material, and on the method for producing the resin beads. As a result, the present inventors have found that by adopting the constitution described below, resin beads that are substantially formed with a natural material and that can provide various types of products, such as a cosmetic imparted with the above-described various properties, can be obtained. That is, the resin beads of the present invention are resin beads formed with a resin containing cellulose as a main component. Then, the resin beads of the present invention have a cumulative 50% particle size on a volume basis of 50 µm or smaller, a degree of sphericity of 0.7 to 1.0, a degree of surface smoothness of 70 to 100%, and a degree of solidity of 50 to 100%. Further, the resin beads of the present invention have a biodegradation rate for 5 days, as measured in accordance with JIS K6950:2000 (ISO 14851: 1999), of 20% or more.

The cumulative 50% particle size (median size; $D_{50}$) on a volume basis of the resin beads is 50 µm or smaller, preferably 30 µm or smaller, more preferably 0.5 to 28 µm, and particularly preferably 1 to 25 µm. By setting $D_{50}$ to the above-described range, the slipperiness and soft-focus performance, which are required in resin beads to be blended in a cosmetic and the like, can effectively be exhibited.

The cumulative 90% particle size ($D_{90}$) on a volume basis of the resin beads is preferably 40 µm or smaller, more preferably 30 µm or smaller, and particularly preferably 5 to 25 µm. Further, the cumulative 10% particle size ($D_{10}$) on a volume basis of the resin beads is preferably 0.1 µm or larger, more preferably 1 µm or larger, and still more preferably 1.5 to 10 µm. Then, the CV value (coefficient of variation) of the particle size of the resin beads is preferably 10 to 90%, more preferably 25 to 75%, and particularly preferably 40 to 60%. By setting $D_{90}$, $D_{10}$, and the CV value to the above-described ranges respectively, smoothness without feeling of a foreign body, which is required in resin beads to be blended in a cosmetic and the like, can be exhibited, and a cosmetic such that getting into wrinkles are suppressed can be made.

The degree of sphericity of the resin beads is 0.7 or more and 1.0 or less, preferably 0.75 to 1.0 or less, more preferably 0.8 to 1.0 or less, and particularly preferably 0.85 to 1.0 or less. By setting the degree of sphericity to the above-described range, favorable tactile impression and spreadability on the skin, which are required in resin beads to be blended in a cosmetic and the like, can effectively be exhibited.

The degree of sphericity, which is an index of whether the resin beads have a perfectly spherical shape or not, can be measured and calculated according to the procedure described below. Firstly, a SEM image of the resin beads, taken with a scanning electron microscope (SEM), is subjected to image analysis to calculate the degree of circularity C for each resin bead from the following formula (1). Then, the arithmetic average value of the degrees of circularity C for 10 or more resin beads arbitrarily selected is defined as the degree of sphericity.

$$C=(4\pi S_1)/(L^2) \quad (1)$$

In the formula (1), $S_1$ represents the area (projected area) of each resin bead in the image, and L represents the length of the outer peripheral part of the resin bead in the image. As the value of the degree of circularity C is closer to 1, the shape of a particle is closer to a perfect sphere.

The degree of surface smoothness of the resin beads is 70 to 100%, preferably 80% to 100%, and more preferably 90 to 100%. By setting the degree of surface smoothness to the above-described range, favorable tactile impression and spreadability on the skin, which are required in resin beads to be blended in a cosmetic and the like, can effectively be exhibited.

The degree of surface smoothness of the resin beads can be measured according to the procedure described below. That is, a SEM image (×5,000) of the resin beads, taken with a scanning electron microscope (SEM), is observed to calculate the degree of smoothness M for each resin bead from the following formula (2). Then, the arithmetic average value of the degrees of smoothness M for 10 or more resin beads arbitrarily selected is defined as the degree of surface smoothness. As the value of the degree of smoothness M is closer to 100, the surface of a particle is closer to be smooth.

$$M=(1-(S_3)/(S_2))\times 100 \quad (2)$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the areas of regions that exist outside the contour of the overlapped circle.

The degree of solidity of the resin beads is 50 to 100% by volume, preferably 60 to 100% by volume, and more preferably 70 to 99% by volume. By setting the degree of solidity within the above-described range, the transparency which is required in resin beads to be blended in a cosmetic and the like can effectively be exhibited. When the degree of solidity of the resin beads is less than 50% by volume, light scattering occurs due to empty regions, so that the transparency is likely to lower. In addition, when the degree of solidity lowers, the oil absorption and strength are changed. For this reason, when resin beads having a low degree of solidity are blended in a product, such as a cosmetic, the product stability may be somewhat lowered.

The degree of solidity of the resin beads can be measured and calculated according to the procedure described below. Firstly, a SEM image of sections of the resin beads, taken with a scanning electron microscope (SEM), is subjected to image analysis to calculate the volume of the part filled with the resin for each resin bead. Then, the average value of the volumes of the parts filled with the resin for 10 or more resin beads arbitrarily selected is defined as the degree of solidity (% by volume).

The biodegradation rate for 5 days of the resin beads is 20% or more, preferably 30% or more, and more preferably 40% or more. The resin beads of the present invention have a high biodegradation rate, as described above, and therefore have excellent biodegradability. For this reason, the resin beads of the present invention are useful as resin beads to be blended in a cosmetic or the like in which exhibiting favorable biodegradability is required. Note that by producing the resin beads according to the production method which will be described later, the resin beads having more excellent biodegradability can be obtained than in the case where the resin beads are produced according to another conventional production method in spite of the fact that the resin beads are produced using the same resin containing cellulose as a main component. The reason has not necessarily been made clear yet.

The biodegradation rate for 5 days of the resin beads is measured in accordance with JIS K6950:2000 (ISO 14851: 1999). More specifically, the biodegradation rate for 5 days of the resin beads is measured and calculated by conducting a test under conditions (measurement of BOD using a closed system oxygen consumption measuring apparatus) shown below.

Inoculum: aerobic reactor sludge in sewage treatment plant that mainly treats domestic wastewater
Reference material: microcrystalline cellulose
Concentration of test material: 100 mg/L
Concentration of reference material: 100 mg/L
Concentration of inoculum: 150 mg/L
Amount of test solution: 300 mL
Test temperature: 25±1° C.
Cultivation period: 30 days The biodegradation rates of the test material and the reference material can be calculated from the following formula.

Biodegradation rate (%)=(BODO−BODB)/ThOD× 100

BODO (mg): biochemical oxygen demand of test material
BODB (mg): average biochemical oxygen demand of reference material
ThOD (mg): Theoretical maximum oxygen demand necessary for oxidizing test material The resin beads are formed with a resin containing cellulose as a main component. The resin for forming the resin beads may contain a cellulose derivative, such as a cellulose ester, in addition to the cellulose. The content of the cellulose in the resin for forming the resin beads is preferably 50 to 100% by mass because the biodegradability of the resin beads is further improved, and is more preferably 60 to 100% by mass, and particularly preferably 70 to 100% by mass. The cellulose may be blended in the resin for forming the resin beads in advance, or may be formed by chemically modifying (for example, hydrolyzing) a cellulose derivative, such as a cellulose ester.

The resin beads may contain at least any one of a pigment and a dye according to the application. To obtain the resin beads containing a pigment or a dye, the suspension may be prepared using, for example, the oil phase further containing at least any one of the pigment and the dye. Examples of the pigment include metal oxides, such as titanium dioxide, zinc oxide, Bengala, yellow iron oxide, and black iron oxide, and besides, Food Yellow No. 4, Food Red No. 202, and Food Blue No. 1, which are Japanese names of certified colors, and carbon black. In addition, extender pigments, such as mica, talc, kaolin, and calcium carbonate, can also be used. Examples of the dye include Food Red No. 104, Food Yellow No. 5, and Food Blue No. 1.

The resin beads preferably contain: a pigment; and at least any one of a surfactant, a dispersant, and a polymer dispersant. In addition, the pigment is preferably a treated pigment treated with at least one selected from the group consisting of a silicone, a fatty acid, a metal salt of a fatty acid, an amino acid, a metal salt of an amino acid, fat and oil, and a lipid.

The resin beads may contain at least any one of an ultraviolet absorbing agent and an ultraviolet scattering agent according to the application. To obtain the resin beads containing an ultraviolet absorbing agent or an ultraviolet scattering agent, the suspension may be prepared using, for example, the oil phase further containing at least any one of the ultraviolet absorbing agent and the ultraviolet scattering agent. Examples of the ultraviolet absorbing agent and the like include fine particle titanium dioxide, fine particle zinc oxide, a cinnamic acid-based ultraviolet absorbing agent, and a dibenzoylmethane-based ultraviolet absorbing agent.

The resin beads may be surface-treated with a silicone, a fatty acid, a metal salt of a fatty acid, an amino acid, a metal salt of an amino acid, oil and fat, a lipid, or the like according to the application.

Next, a method for producing the above-described resin beads will be described. The method for producing resin beads of the present invention is a method for producing the above-described resin beads and includes a step (suspension preparation step) of mixing an oil phase (first liquid) containing a cellulose ester and an organic solvent that dissolves the cellulose ester with an aqueous phase (second liquid) containing a dispersion stabilizer, thereby preparing a suspension containing oil droplets containing the cellulose ester and the organic solvent.

In the suspension preparation step, the oil phase containing a cellulose ester and an organic solvent that dissolves the cellulose ester is mixed with an aqueous phase containing a dispersion stabilizer. By mixing and, if necessary, stirring the oil phase and the aqueous phase, a suspension in which oil droplets containing the cellulose ester and the organic solvent are dispersed in water can be obtained. The oil droplets are present in a dispersed state in water, and therefore the organic solvent in the oil droplets transfers gradually into water. Then, the oil droplets contract accompanying the transfer of the organic solvent, so that the cellulose ester dissolved in the organic solvent precipitates gradually. The precipitated cellulose ester grows while retaining smooth surfaces. Finally, the precipitated cellulose ester is fixed, and resin particles which are precursors for substantially solid resin beads are formed. Whether the contraction of the oil droplets has occurred or not can be decided by analyzing an image observed using an optical microscope, an electron microscope, or the like. When such contraction of the oil droplets occurs, resin beads which have high sphericity (degree of sphericity), which are substantially solid, which have smooth surfaces, and which have a desired particle size can thereby be obtained.

The cellulose ester is used, as a natural cellulose derivative, for products, such as a cosmetic. As the cellulose ester, at least one selected from a cellulose organic acid ester and a cellulose phosphoric acid ester is preferably used. More specifically, as the cellulose ester, at least one selected from the group consisting of cellulose acetate, cellulose propionate, cellulose acetate propionate, cellulose butyrate, and cellulose acetate butyrate is preferably used.

By hydrolyzing, under an appropriate condition, at least part of ester bonds in the cellulose ester contained in the resin for forming resin particles, resin beads having a degree of sphericity, a degree of surface smoothness, and a degree of solidity which are suitable for the cosmetic application can be obtained. That is, by appropriately controlling the conditions in hydrolysis, defects which are likely to occur in preparing the resin beads containing a resin containing cellulose as a main component are suppressed and resin beads that can suitably be blended in a cosmetic and the like can be produced.

As the cellulose ester, a cellulose ester in which the content of an acyl group, such as an acetyl group, a propionyl group, and a butyroyl group, is 60% by mass or less is preferably used.

Among others, cellulose acetate or cellulose acetate propionate in which the content of the acyl group is 60% by mass or less is preferably used. In addition, a cellulose ester such that the viscosity of a 6%-by-mass acetone solution is 200 mPa·s or lower is preferably used. When these cellulose esters are used, a defect and the like are unlikely to occur in the particle size distribution and tactile impression of resin beads to be obtained, and resin beads that can suitably be blended in a cosmetic and the like can be obtained more easily.

As the organic solvent (first organic solvent) contained in the oil phase, a known organic solvent which can dissolve the cellulose ester can be used. As the specific examples of the organic solvent, ester-based solvents, such as methyl formate, ethyl formate, methyl acetate, ethyl acetate, and butyl acetate; ketone-based solvents, such as acetone, methyl ethyl ketone, methyl isobutyl ketone, and cyclohexanone; alcohols, such as ethanol and n-butanol; ether-based solvents, such as ethyl cellosolve, butyl cellosolve, and ethylene glycol diethyl ether; glycol ether-based solvents, such as dipropylene glycol monomethyl ether; glycol ester-based solvents, such as propylene glycol monomethyl ether acetate; chlorine-based solvents, such as methylene chloride, chloroform, and tetrachloroethane; nitromethane; propylene carbonate, and the like can be used. These organic solvents can be used singly, or two or more of these organic solvents can be used in combination.

The organic solvent is preferably a ketone-based solvent, an ester-based solvent, an alcohol, a glycol, an ether-based solvent, a halogenated alkyl, or a nitrated alkyl. Among others, the organic solvent is more preferably methyl ethyl ketone, ethyl acetate, butanol, propylene glycol monobutyl ether, propyl acetate, or propylene glycol monomethyl ether acetate.

The organic solvent in the oil droplets contained in the suspension transfers gradually into the aqueous phase. However, when the water-solubility of the organic solvent is too high, the organic solvent is likely to transfer rapidly from the oil droplets into the aqueous phase, and therefore the resin particles which are formed by the contraction of the oil droplets and which are precursors for the resin beads may be unlikely to have a perfectly spherical shape, or a smooth surface may be unlikely to be formed. In addition, when the water-solubility of the organic solvent is too high, the aqueous phase is likely to penetrate partially into the oil droplets, so that solid resin particles may be unlikely to be formed. On the other hand, when the water-solubility of the organic solvent is too low, there is a tendency that the transfer speed of the organic solvent from the oil droplets into the aqueous phase is lowered and a large amount of aqueous phase needs to be used, so that the resin beads may be disadvantageous in terms of production costs. In addition, when the water-solubility of the organic solvent is too low, the organic solvent may be likely to be left in the resin beads. For this reason, the solubility (water-solubility) of the organic solvent to 100 g of water at 25° C. is 0.1 to 50.0 g, preferably 0.5 to 40.0 g, and more preferably 1.0 to 30.0 g.

The liquid amount of the organic solvent contained in the oil phase (first liquid) is preferably 2.0 times or more, more preferably 2.5 to 15.0 times, based on the amount of the cellulose ester on a mass basis. If the liquid amount of the organic solvent in the oil phase is too small, the cellulose ester is likely to precipitate rapidly when the organic solvent in the oil droplets transfers into the aqueous phase. For this reason, resin beads to be obtained may be unlikely to have a perfectly spherical shape, or a smooth surface may be unlikely to be formed.

The aqueous phase that is used in the suspension preparation step is a liquid (second liquid) in which a dispersion stabilizer is dissolved in water, such as deionized water. As the dispersion stabilizer, water-soluble polymers, such as water-soluble cellulose, polyvinyl alcohol, and sodium polyacrylate; and inorganic salts, such as hydroxyapatite, tribasic calcium phosphate, and calcium carbonate, can be used. These dispersion stabilizers can be used singly, or two or more of these dispersion stabilizers can be used in combination. Among these dispersion stabilizers, a water-soluble polymer, such as water-soluble cellulose, polyvinyl alcohol, or sodium polyacrylate, is preferably used.

To suppress break or coalescence of the oil droplets in the suspension during transportation, it is preferable that the type and concentration of the dispersion stabilizer which is used in the aqueous phase are set appropriately. The content of the dispersion stabilizer in the aqueous phase is preferably 30% by mass or less, more preferably 1 to 20% by mass.

It is preferable that the aqueous phase further contain a second organic solvent. The organic solvent (first organic solvent) in the oil phase may transfer rapidly into the aqueous phase depending on the type. Accordingly, by mixing the aqueous phase containing the second organic solvent with the oil phase, the rapid transfer of the first organic solvent in the oil phase into the aqueous phase can be suppressed, so that resin beads having a higher degree of sphericity and having a smoother surface can be produced. As the second organic solvent, any of the above-described organic solvents (first organic solvents) which can be used in the oil phase, including preferred first organic solvents, can be used. Note that the first organic solvent and the second organic solvent may be of the same types or of different types.

In the suspension preparation step, the suspension is prepared by mixing the oil phase and the aqueous phase. To mix the oil phase and the aqueous phase, the oil phase may be added to the aqueous phase under stirring, or the aqueous phase may be added to the oil phase under stirring. The particle sizes of the oil droplets to be formed are preferably adjusted using an emulsification apparatus, such as a disper or a homogenizer, as necessary. The particle sizes of the oil droplets to be formed can easily be adjusted by, for example, changing the number of revolutions of a homogenizer to adjust the shear force. As a result, the particle sizes of the resin beads to be obtained can appropriately be adjusted in such a way as to fall within a desired range.

The liquid amount of the aqueous phase is preferably set to 3.0 times or less, and more preferably 0.2 to 2.8 times, based on the liquid amount of the oil phase on a mass basis. By setting the liquid amount of the aqueous phase to the above-described range, the rapid transfer of the organic solvent in the oil droplets into the aqueous phase can be suppressed, so that resin beads having a higher degree of sphericity and having a smoother surface can be produced.

The method for producing resin beads of the present invention further includes a step (contraction step) of adding water to the suspension, thereby contracting the oil droplets and forming resin particles. By adding water to the suspension, the oil droplets in the suspension can be contracted more quickly and the resin particles which are precursors for the resin beads can be formed. The liquid amount of water to be added to the suspension is preferably 0.5 times or more, more preferably 1 to 100 times, based on the liquid amount of the suspension on a mass basis.

In the contraction step, water is preferably added to the suspension over a time of about 10 minutes or longer. By adding water over a time of 10 minutes or longer, the rapid transfer of the organic solvent in the oil droplets into the aqueous phase can be suppressed, so that resin particles and resin beads having a higher degree of sphericity and having a smoother surface can be produced. Specifically, water is preferably added to the suspension over 30 minutes or longer, water is more preferably added over 45 minutes or longer, and water is particularly preferably added over 60 to 300 minutes.

The method for producing resin beads of the present invention further includes a step (hydrolysis step) of treating the resin particles formed in the above-described contraction step under an acidic condition, or an alkaline condition of a pH of 13 or lower, thereby hydrolyzing at least part of ester bonds in the cellulose ester. Thereby, resin beads which are formed with a resin containing cellulose as a main component, which have a desired degree of sphericity, degree of surface smoothness, and degree of solidity, and which exhibit favorable biodegradability can be obtained.

In the case where the resin particles are treated under an alkaline condition, pH is 13 or lower, preferably 8 to 13. When pH is higher than 13, cellulose produced by the hydrolysis of the ester bonds is likely to aggregate, so that resin beads having desired properties cannot be obtained. In addition, in the case where the resin particles are treated under an acidic condition, pH is preferably 1.5 to 6, more preferably 1.8 to 5.5.

The temperature during the hydrolysis is preferably set to 80° C. or lower. That is, at least part of the ester bonds in the cellulose ester is preferably hydrolyzed by treating the resin particles under a temperature condition of 80° C. or lower, more preferably under a temperature condition of 0 to 70° C., and particularly preferably at 10 to 60° C. The degree (degree of progress) of the hydrolysis of the ester bonds can be monitored by infrared spectroscopy (IR) whenever necessary. Neutralization may be performed by adding an acid or an alkali after checking the degree (degree of progress) of the hydrolysis.

After the hydrolysis, unnecessary components are removed by, for example, subjecting the produced resin beads to filtration and washing. Subsequently, washing is repeated multiple times as necessary, and then drying and a disintegration treatment are performed, and thereby intended resin beads can be obtained. Further, if necessary, the resin particles may be surface-treated by an ordinary method using a silicone, a fatty acid, a metal salt of a fatty acid, an amino acid, a metal salt of an amino acid, fat and oil, a lipid, or the like.

The above-described resin beads are resin particles which have high sphericity (degree of sphericity), which are solid, which have a smooth surface and exhibit excellent biodegradability, and which are obtained using a natural material as a constituent material. For this reason, various types of products, such as a cosmetic, a dermatological preparation, a paint, a shaped article, a film, a coating agent, and a resin composition, which are imparted with excellent tactile impression, spreadability on the skin, and product stability, can be provided without using resin particles composed of a synthetic material derived from petroleum by allowing the above-described resin beads to be contained in the products.

EXAMPLES

Hereinafter, the present invention will specifically be described based on Examples, but the present invention is not limited to these Examples. Note that "parts" and "%" in Examples and Comparative Examples are on a mass basis unless otherwise noted.
<Production of Resin Beads>

Example 1

An oil phase was prepared by dissolving 250 parts of cellulose acetate (trade name "CA-398-3," manufactured by Eastman Chemical Company, content ratio of acetyl group: 39.8%) in 2,250 parts of ethyl acetate (water-solubility: 8 g/100 g). In addition, an aqueous phase was prepared by dissolving 200 parts of polyvinyl alcohol in 2,300 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,800 rpm for 10 minutes to obtain a suspension in which oil droplets were dispersed uniformly. The volume average particle size of the oil droplets, as measured through observation with an optical microscope and image analysis, was 20 μm.

Figure 1:
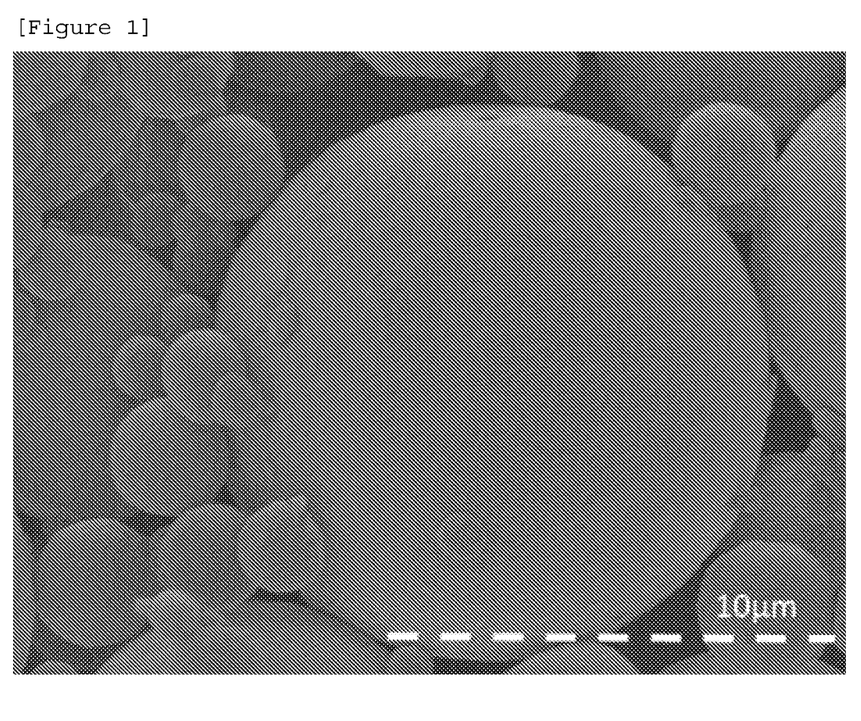
FIG. 1 is an electron micrograph showing a state of surfaces of resin beads produced in Example 1.
Figure 2:
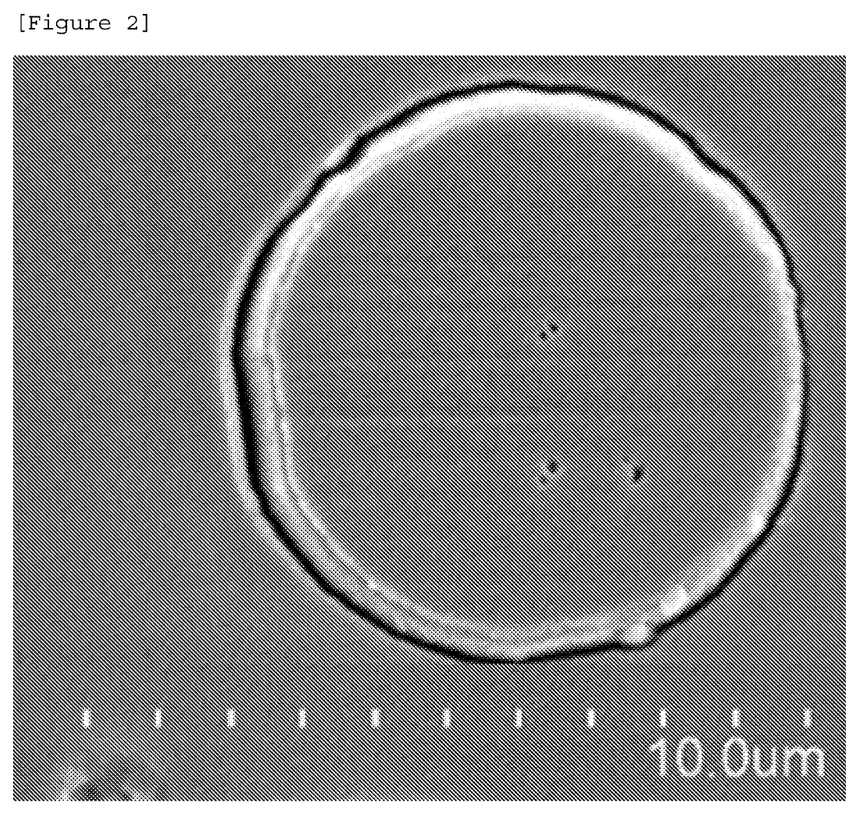
FIG. 2 is an electron micrograph showing a state of a section of a resin bead produced in Example 1.

A resin particle dispersion was obtained by pouring 112,500 parts of ion-exchanged water into the obtained suspension over 75 minutes while the suspension was being stirred using the dissolver at 500 rpm. The resin particles were subjected to filtration and washing, and then deflocculated in ion-exchanged water and stirred. Resin particles obtained through filtration and washing were dispersed in 2,500 parts of ion-exchanged water. Sodium hydroxide was added to adjust pH of the dispersion to 13.0 or lower and the dispersion was heated to 60° C. to perform hydrolysis reaction. After the hydrolysis reaction was completed, the reaction solution was neutralized with hydrochloric acid. The product was subjected to filtration and washing, and then deflocculated in ion-exchanged water. Further, the product was subjected to filtration and washing, and then subjected to drying and a disintegration treatment to obtain resin beads. FIG. 1 shows an electron micrograph showing a state of surfaces of the obtained resin beads. Further, FIG. 2 shows an electron micrograph showing a state of a section of an obtained resin bead.

Example 2

An oil phase was prepared by dissolving 250 parts of cellulose acetate propionate (trade name "CAP-482-0.5," manufactured by Eastman Chemical Company, total content ratio of acetyl group and propionyl group: 46.5%) in 1,000 parts of ethyl acetate (water-solubility: 8 g/100 g). In addition, an aqueous phase was prepared by dissolving 100 parts of polyvinyl alcohol in 1,088 parts of ion-exchanged water, and adding 62.5 parts of ethyl acetate thereto and stirring the resultant mixture. The oil phase was added to and mixed with the prepared aqueous phase, and the resultant mixture was stirred using a dissolver at 1,000 rpm for 3 minutes. The mixture was further stirred using the dissolver at 1,500 rpm for 5 minutes to obtain a suspension in which oil droplets were dispersed uniformly. The volume average particle size of the oil droplets, as measured through observation with an optical microscope and image analysis, was 22 μm.

A resin particle dispersion was obtained by pouring 21,250 parts of ion-exchanged water into the obtained suspension over 60 minutes while the suspension was being stirred using the dissolver at 500 rpm. The resin particles were subjected to filtration and washing, and then deflocculated in ion-exchanged water and stirred. The resultant mixture was subjected to filtration and washing, and then drying and a disintegration treatment were performed to obtain resin particles. The obtained resin particles were dispersed in 5,000 parts of ion-exchanged water. Sodium hydroxide was added to adjust pH of the dispersion to 13.0 or lower and the dispersion was heated to 40° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain resin beads.

Example 3

An oil phase was prepared by dissolving 50 parts of cellulose acetate propionate (trade name "CAP-504-0.2," manufactured by Eastman Chemical Company, total content ratio of acetyl group and propionyl group: 43.0%) and 50 parts of cellulose acetate (trade name "CA-398-6," manufactured by Eastman Chemical Company, content ratio of acetyl group: 39.8%) in 1,000 parts of isopropyl acetate (water-solubility: 4 g/100 g). In addition, an aqueous phase was prepared by dissolving 150 parts of polyvinyl alcohol in 1,350 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,600 rpm for 7 minutes to obtain a suspension in which oil droplets were dispersed uniformly. The volume average particle size of the oil droplets, as measured through observation with an optical microscope and image analysis, was 12 μm.

A resin particle dispersion was obtained by pouring 52,400 parts of ion-exchanged water into the obtained suspension over 120 minutes while the suspension was being stirred using the dissolver at 500 rpm. The resin particles were subjected to filtration and washing, and then deflocculated in ion-exchanged water and stirred. Resin particles obtained through filtration and washing were dispersed in 5,000 parts of ion-exchanged water. Diluted hydrochloric acid was added to adjust pH of the dispersion to 2.0 and the dispersion was heated to 40° C. to perform hydrolysis reaction. After the hydrolysis reaction was completed, the reaction solution was neutralized with sodium hydroxide. The product was subjected to filtration and washing, and then deflocculated in ion-exchanged water. Further, the product was subjected to filtration and washing, and then subjected to drying and a disintegration treatment to obtain resin beads.

Example 4

An oil phase was prepared by dissolving 250 parts of cellulose acetate (trade name "CA-398-10," manufactured by Eastman Chemical Company, content ratio of acetyl group: 39.8%) in 2,750 parts of ethyl acetate (water-solubility: 8 g/100 g). In addition, an aqueous phase was prepared by dissolving 180 parts of polyvinyl alcohol in 2,820 parts of ion-exchanged water. The oil phase was added to and mixed with the prepared aqueous phase, and the resultant mixture was stirred using a dissolver at 1,000 rpm for 3 minutes. The mixture was further stirred using the dissolver at 2,000 rpm for 5 minutes to obtain a suspension in which oil droplets were dispersed uniformly. The volume average particle size of the oil droplets, as measured through observation with an optical microscope and image analysis, was 18 μm.

A resin particle dispersion was obtained by pouring 40,000 parts of ion-exchanged water into the obtained suspension over 90 minutes while the suspension was being stirred using the dissolver at 500 rpm. The resin particles were subjected to filtration and washing, and then deflocculated in ion-exchanged water and stirred. Resin particles obtained through filtration and washing were dispersed in 2,500 parts of ion-exchanged water. Sodium hydroxide was added to adjust pH of the dispersion to 13.0 or lower and the dispersion was heated to 55° C. to perform hydrolysis reaction until ester bonds corresponding to 90% of the cellulose acetate were decomposed, and then the reaction solution was neutralized with hydrochloric acid. The product was subjected to filtration and washing, and then deflocculated in ion-exchanged water. Further, the product was subjected to filtration and washing, and then subjected to drying and a disintegration treatment to obtain resin beads.

Example 5

An oil phase was prepared by dissolving 78 parts of cellulose acetate propionate (trade name "CAP-504-0.2," manufactured by Eastman Chemical Company, total content ratio of acetyl group and propionyl group: 43.0%) in 900 parts of 1-butanol (water-solubility: 8 g/100 g). To the prepared oil phase, 20 parts of fine particle titanium oxide (trade name "MT-100TV," manufactured by TAYCA CORPORATION), treated with a fatty acid, and 2 parts of an acrylic silicone dispersant (trade name "KP-578," manufactured by Shin-Etsu Chemical Co., Ltd.) were added, and the resultant mixture was mixed to disperse the fine particle titanium oxide in the oil phase. In addition, an aqueous phase was prepared by dissolving 80 parts of polyacrylic acid in 920 parts of ion-exchanged water. The oil phase was added to and mixed with the prepared aqueous phase, and the resultant mixture was stirred using a dissolver at 1,000 rpm for 3 minutes. The mixture was further stirred using the dissolver at 2,200 rpm for 20 minutes to obtain a suspension in which oil droplets were dispersed uniformly. The volume average particle size of the oil droplets, as measured through observation with an optical microscope and image analysis, was 8 μm.

A resin particle dispersion was obtained by pouring 43,000 parts of ion-exchanged water into the obtained suspension over 180 minutes while the suspension was being stirred using the dissolver at 500 rpm. The resin particles were subjected to filtration and washing, and then deflocculated in ion-exchanged water and stirred. The resultant mixture was subjected to filtration and washing, and then drying and a disintegration treatment were performed to obtain resin particles. The obtained resin particles were dispersed in 5,000 parts of ion-exchanged water. Sodium hydroxide was added to adjust pH of the dispersion to 13.0 or lower and the dispersion was heated to 55° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain resin beads.

Comparative Example 1

Cellulose fine particles (trade name "CELLULOBEADS D-5," manufactured by DAITO KASEI KOGYO CO., LTD.) were used as resin beads of Comparative Example 1.

Comparative Example 2

An oil phase was prepared by dissolving 70 parts of cellulose acetate (trade name "CA-398-3," manufactured by Eastman Chemical Company, content ratio of acetyl group: 39.8%) in 630 parts of acetone (water-solubility: co g/100 g). In addition, an aqueous phase was prepared by dissolving 70 parts of polyvinyl alcohol in 630 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,700 rpm for 50 minutes to obtain a suspension in which oil droplets were dispersed uniformly. The volume average particle size of the oil droplets, as measured through observation with an optical microscope and image analysis, was 120 μm.

A resin particle dispersion was obtained by pouring 12,600 parts of ion-exchanged water into the obtained suspension over 60 minutes while the suspension was being stirred using the dissolver at 500 rpm. The resin particles were subjected to filtration and washing, and then deflocculated in ion-exchanged water and stirred. Resin particles obtained through filtration and washing were dispersed in 2,300 parts of ion-exchanged water. Sodium hydroxide was added to adjust pH of the dispersion to 13.0 or lower and the dispersion was heated to 30° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain resin beads.

Comparative Example 3

An oil phase was prepared by dissolving 70 parts of acetyl cellulose (trade name "CA-398-6," manufactured by Eastman Chemical Company, content ratio of acetyl group: 39.8%) in 770 parts of ethyl acetate (water-solubility: 8 g/100 g). In addition, an aqueous phase was prepared by dissolving 24 parts of polyvinyl alcohol in 776 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,500 rpm for 10 minutes to obtain a suspension in which oil droplets were dispersed uniformly. The volume average particle size of the oil droplets, as measured through observation with an optical microscope and image analysis, was 38 μm.

A resin particle dispersion was obtained by pouring the obtained suspension into 36,860 parts of ion-exchanged water over 60 minutes while the ion-exchanged water was being stirred using the dissolver at 500 rpm. The resin particles were subjected to filtration and washing, and then deflocculated in ion-exchanged water and stirred. Resin particles obtained through filtration and washing were dispersed in 1,400 parts of ion-exchanged water. Sodium hydroxide was added to adjust pH of the dispersion to 13.0 or lower and the dispersion was heated to 40° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain resin beads.

Comparative Example 4

An oil phase was prepared by dissolving 100 parts of cellulose acetate propionate (trade name "CAP-482-0.5," manufactured by Eastman Chemical Company, total content ratio of acetyl group and propionyl group: 46.5%) in 900 parts of ethyl acetate (water-solubility: 8 g/100 g). In addition, an aqueous phase was prepared by dissolving 50 parts of polyvinyl alcohol in 950 parts of ion-exchanged water. The oil phase was added to and mixed with the prepared aqueous phase, and the resultant mixture was stirred using a dissolver at 1,000 rpm for 3 minutes. The mixture was further stirred using the dissolver at 1,750 rpm for 10 minutes to obtain a suspension in which oil droplets were dispersed uniformly. The volume average particle size of the oil droplets, as measured through observation with an optical microscope and image analysis, was 16 μm.

A resin particle dispersion was obtained by pouring 28,000 parts of ion-exchanged water into the obtained suspension over 120 minutes while the suspension was being stirred using the dissolver at 500 rpm. The resin particles were subjected to filtration and washing, and then deflocculated in ion-exchanged water and stirred. Resin particles obtained through filtration and washing were dispersed in 3,000 parts of ion-exchanged water. Sodium hydroxide was added to adjust pH of the dispersion to 13.5 and the dispersion was heated to 45° C. to perform hydrolysis reaction. After the hydrolysis reaction was completed, the reaction solution was neutralized with acetic acid. The product was subjected to filtration and washing, and then deflocculated in ion-exchanged water. Further, the product was subjected to filtration and washing, and then subjected to drying and a disintegration treatment to obtain resin beads.

<Evaluation of Resin Beads>
(Particle Size and Coefficient of Variation (CV Value))

The cumulative 50% particle size ($D_{50}$) on a volume basis, cumulative 10% particle size ($D_{10}$) on a volume basis, and cumulative 90% particle size ($D_{90}$) on a volume basis were measured of the resin beads using Coulter Counter (manufactured by Beckman Coulter, Inc.), and the coefficient of variation (CV value) of the particle size was calculated. Results are shown in Table 1.

(Degree of Sphericity)

A SEM image of the resin beads, taken with a scanning electron microscope (SEM), was subjected to image analysis to calculate the degree of circularity C for each resin bead from the following formula (1). Then, the arithmetic average value of the degrees of circularity C for 10 or more resin beads arbitrarily selected was defined as the degree of sphericity. Results are shown in Table 1.

$$C=(4\pi S_1)/(L^2) \tag{1}$$

In the formula (1), $S_1$ represents the area (projected area) of each resin bead in the image, and L represents the length of the outer peripheral part of the resin bead in the image. As the value of the degree of circularity C is closer to 1, the shape of a particle is closer to a perfect sphere.

(Degree of Surface Smoothness)

A SEM image (×5,000) of the resin beads, taken with a scanning electron microscope (SEM), was observed to calculate the degree of smoothness M for each resin bead from the following formula (2). Then, the arithmetic average value of the degrees of smoothness M for 10 or more resin beads arbitrarily selected was defined as the degree of surface smoothness. Results are shown in Table 1. As the value of the degree of smoothness M is closer to 100, the surface of a particle is closer to be smooth.

$$M=(1-(S_3)/(S_2))\times 100 \tag{2}$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the areas of regions that exist outside the contour of the overlapped circle.

(Degree of Solidity)

A SEM image of sections of the resin beads, taken with a scanning electron microscope (SEM), was subjected to image analysis to calculate the volume of the part filled with the resin for each resin bead. Then, the average value of the volumes of the parts filled with the resin for 10 or more resin beads arbitrarily selected was defined as the degree of solidity (% by volume). Results are shown in Table 1.

(Content of Cellulose)

The content of the cellulose in the resin forming the resin beads was measured by infrared absorption spectroscopy. Specifically, some mixtures each containing the cellulose and the cellulose ester at an arbitrary ratio were prepared to make a calibration curve based on the peak intensity of the carbonyl group of the cellulose ester at around 1750 cm$^{-1}$. Then, the content of the cellulose in the resin forming the resin beads was calculated using this calibration curve. Calculated contents of the cellulose are shown in Table 1.

TABLE 1

|  | $D_{50}$ (μm) | Degree of sphericity | $D_{90}$ (μm) | $D_{10}$ (μm) | CV value (%) | Degree of surface smoothness (%) | Degree of solidity (%) | Content (%) of cellulose |
|---|---|---|---|---|---|---|---|---|
| Example 1 | 10.0 | 0.96 | 18.0 | 5.0 | 51 | 92 | 94 | 100 |
| Example 2 | 12.7 | 0.95 | 23.1 | 7.4 | 47 | 96 | 89 | 100 |
| Example 3 | 6.0 | 0.99 | 10.5 | 3.2 | 46 | 98 | 96 | 100 |
| Example 4 | 8.0 | 0.95 | 14.1 | 4.1 | 51 | 96 | 85 | 90 |
| Example 5 | 4.0 | 0.98 | 7.2 | 2.2 | 48 | 97 | 97 | 100 |
| Comparative Example 1 | 13.0 | 0.67 | 27.0 | 9.1 | 50 | 62 | 66 | 100 |

TABLE 1-continued

|  | $D_{50}$ (μm) | Degree of sphericity | $D_{90}$ (μm) | $D_{10}$ (μm) | CV value (%) | Degree of surface smoothness (%) | Degree of solidity (%) | Content (%) of cellulose |
|---|---|---|---|---|---|---|---|---|
| Comparative Example 2 | 120.0 | 0.42 | 223.0 | 69.0 | 69 | 40 | 48 | 100 |
| Comparative Example 3 | 17.5 | 0.50 | 46.4 | 8.4 | 70 | 51 | 88 | 100 |
| Comparative Example 4 | 14.7 | 0.54 | 30.1 | 10.3 | 61 | 54 | 74 | 100 |

(Tactile Impression)

Sensory evaluation on the tactile impression for the resin beads by a panel test of ten people was performed. The "slickness" and the "spreadability on the skin" were totally decided when the resin beads were touched, and the tactile impression for the resin beads was graded on a scale of 1 to 5 according to the evaluation criteria shown below to calculate the average mark in ten people. Results are shown in Table 2.

5: Excellent
4: Above average
3: Average
2: Below average
1: Poor (Biodegradability)

The biodegradability (after 5 days) of the resin beads was measured and calculated in accordance with JIS K6950: 2000 (ISO 14851:1999). Results are shown in Table 2.

TABLE 2

|  | Tactile impression | Biodegradation rate (%) |
|---|---|---|
| Example 1 | 4.5 | 49 |
| Example 2 | 4.4 | 48 |
| Example 3 | 4.7 | 49 |
| Example 4 | 4.7 | 41 |
| Example 5 | 4.5 | 49 |
| Comparative Example 1 | 2.1 | 31 |
| Comparative Example 2 | 1.2 | 43 |
| Comparative Example 3 | 2.3 | 45 |
| Comparative Example 4 | 2.0 | 44 |

<Production of Cosmetic>
(Cosmetic-1)

Cosmetic-1 was produced by mixing components which had conventionally been used as raw materials for cosmetics. Specifically, silicone-treated powders (mica, talc, fine particle titanium oxide, and barium sulfate) and the resin beads were first blended according to the blending amounts shown in Table 3, and a resultant mixture was mixed until it became uniform to obtain a powder mixture. Subsequently, a mixture (additional components) obtained by mixing Vaseline, squalane, and glyceryl trioctanoate was added to the powder mixture, and a resultant mixture was mixed until it became uniform. Thereafter, the mixture was filled in a container, and press shaping was performed as necessary to obtain cosmetic-1.

TABLE 3

|  | Component name | Blending amount (parts) |
|---|---|---|
| Additional components | Vaseline | 2.5 |
|  | Squalane | 2.5 |
|  | Glyceryl trioctanoate | 2.5 |

TABLE 3-continued

|  | Component name | Blending amount (parts) |
|---|---|---|
| Powder mixture | Silicone-treated mica | 40.0 |
|  | Silicone-treated talc | 33.0 |
|  | Silicone-treated fine particle titanium oxide | 5.0 |
|  | Silicone-treated barium sulfate | 10.0 |
|  | Resin beads | 4.5 |

(Cosmetic-2)

Cosmetic-2, which is a Sun-Cut milky lotion, was produced by mixing components which had conventionally been used as raw materials for cosmetics. Specifically, a silicone oil, an ultraviolet protective agent, an emulsifier, a dispersant, isotridecyl isononanoate, and the resin beads were first blended according to the blending amounts shown in Table 4 and mixed to prepare oil phase components. Further, purified water, dipropylene glycol, sodium chloride, and sodium citrate were blended according to the blending amounts shown in Table 4 and mixed to prepare aqueous phase components. Subsequently, the aqueous phase components were added to the prepared oil phase components while the oil phase components were being stirred, and thus emulsification was performed to obtain cosmetic-2.

TABLE 4

|  | Component name | Blending amount (parts) |
|---|---|---|
| Aqueous phase components | Purified water | 16.3 |
|  | Dipropylene glycol | 2.5 |
|  | Sodium chloride | 1.0 |
|  | Sodium citrate | 0.2 |
| Oil phase components | Silicone oil | 30.0 |
|  | Ultraviolet protective agent | 35.0 |
|  | Emulsifier | 5.0 |
|  | Dispersant | 1.0 |
|  | Isotridecyl isononanoate | 4.0 |
|  | Resin beads | 5.0 |

<Evaluation of Cosmetic-1>
(Tactile Impression and Spreadability on Skin)

Sensory evaluation on the tactile impression and the spreadability on the skin for cosmetic-1 by a panel test of ten people was performed. The "tactile impression" and the "spreadability on the skin" were decided and graded on a scale of 1 to 5 according to the evaluation criteria shown below to calculate the average mark in ten people. Results are shown in Table 5.

5: Excellent
4: Above average
3: Average
2: Below average
1: Poor

TABLE 5

| Cosmetic-1 | Resin beads | Tactile impression | Spreadability on skin |
|---|---|---|---|
| Example A1 | Example 1 | 4.7 | 4.7 |
| Example A2 | Example 2 | 4.8 | 4.8 |
| Example A3 | Example 3 | 4.6 | 4.6 |
| Example A4 | Example 4 | 4.7 | 4.4 |
| Example A5 | Example 5 | 4.4 | 4.5 |
| Comparative Example A1 | Comparative Example 1 | 1.9 | 2.1 |
| Comparative Example A2 | Comparative Example 2 | 1.3 | 1.4 |
| Comparative Example A3 | Comparative Example 3 | 1.6 | 1.7 |
| Comparative Example A4 | Comparative Example 4 | 1.7 | 1.8 |

<Evaluation of Cosmetic-2>
(Tactile Impression, Spreadability on Skin, and Transparency)

Sensory evaluation on the tactile impression, the spreadability on the skin, and the transparency for cosmetic-2 by a panel test of ten people was performed. The "tactile impression," the "spreadability on the skin," and the "transparency" were decided and graded on a scale of 1 to 5 according to the evaluation criteria shown below to calculate the average mark in ten people. Results are shown in Table 6.

5: Excellent
4: Above average
3: Average
2: Below average
1: Poor

TABLE 6

| Cosmetic-2 | Resin beads | Tactile impression | Spreadability on skin | Transparency |
|---|---|---|---|---|
| Example B1 | Example 1 | 4.6 | 4.8 | 4.7 |
| Example B2 | Example 2 | 4.7 | 4.8 | 4.7 |
| Example B3 | Example 3 | 4.8 | 4.8 | 4.6 |
| Example B4 | Example 4 | 4.6 | 4.6 | 4.5 |
| Example B5 | Example 5 | 4.6 | 4.5 | 4.8 |
| Comparative Example B1 | Comparative Example 1 | 2.1 | 1.6 | 2.8 |
| Comparative Example B2 | Comparative Example 2 | 1.1 | 1.1 | 2.5 |
| Comparative Example B3 | Comparative Example 3 | 1.8 | 1.7 | 2.8 |
| Comparative Example B4 | Comparative Example 4 | 1.9 | 1.7 | 2.7 |

As shown in Tables 5 and 6, it is understood that cosmetics having excellent tactile impression, spreadability on the skin, and transparency, were able to be produced by using the resin beads of Examples. Further, it was ascertained that properties, such as excellent tactile impression, transparency, and spreadability, were also able to be imparted not only to a cosmetic but also to various types of products, such as a dermatological preparation, a paint, a shaped article, a film, a coating agent, and a resin composition, by using the resin beads of Examples.

INDUSTRIAL APPLICABILITY

The resin beads of the present invention have properties equal to or superior to those of the resin beads formed with a synthetic material derived from petroleum. For this reason, by using the resin beads of the present invention, products, such as a cosmetic exhibiting satisfactory tactile impression, having favorable spreadability on the skin, having transparency, and having favorable biodegradability, can be provided without using resin beads formed with a synthetic material derived from petroleum. Accordingly, the resin beads of the present invention are useful as a constituent material for various types of products, such as, for example, a cosmetic, a dermatological preparation, a paint, a shaped article, a film, a coating agent, and a resin composition.

The invention claimed is:

1. A method for producing resin beads formed with a resin comprising cellulose, being a method for producing the resin beads, the method comprising:
mixing an oil phase comprising a cellulose ester and an organic solvent that dissolves the cellulose ester and has a solubility to 100 g of water at 25° C. in a range from 0.1 to 50.0 g with an aqueous phase comprising a dispersion stabilizer, thereby preparing a suspension comprising oil droplets comprising the cellulose ester and the organic solvent;
adding water to the suspension, thereby contracting the oil droplets and forming resin particles; and
treating the resin particles under an acidic condition, or an alkaline condition of a pH in a range of 13 or lower, thereby hydrolyzing at least part of ester bonds in the cellulose ester,
wherein the resin beads have a cumulative 50% particle size on a volume basis in a range of 50 µm or smaller, a degree of sphericity in a range from 0.7 to 1.0, a degree of surface smoothness in a range from 70 to 100%, a degree of solidity in a range from 50 to 100%, and a biodegradation rate for 5 days, as measured in accordance with JIS K6950:2000 (ISO 14851:1999), in a range of 20% or more, and a content of the cellulose in the resin beads is in a range from 90 to 100% by mass.

2. The method for producing resin beads according to claim 1, wherein the water is added to the suspension over a time in a range of 10 minutes or longer.

3. The method for producing resin beads according to claim 1, wherein a liquid amount of the water to be added to the suspension is in a range of 0.5 times or more based on a liquid amount of the suspension on a mass basis.

4. The method for producing resin beads according to claim 1, wherein the cellulose ester is at least one material selected from the group consisting of a cellulose organic acid ester and a cellulose phosphoric acid ester.

5. The method for producing resin beads according to claim 1, wherein the cellulose ester is at least one material selected from the group consisting of cellulose acetate, cellulose propionate, cellulose acetate propionate, cellulose butyrate, and cellulose acetate butyrate.

6. The method for producing resin beads according to claim 1, wherein the dispersion stabilizer is a water-soluble polymer.

7. The method for producing resin beads according to claim 1, wherein the resin particles are treated under a temperature condition in a range of 80° C. or lower, thereby hydrolyzing at least part of the ester bonds in the cellulose ester.

* * * * *